United States Patent [19]

Mack et al.

[11] Patent Number: Plant 6,621

[45] Date of Patent: Feb. 21, 1989

[54] CHRYSANTHEMUM PLANT NAMED TARGET

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 97,586

[22] Filed: Sep. 16, 1987

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Target particularly characterized by its flat capitulum form; decorative capitulum type; yellow ray floret color; diameter across face of capitulum of up to 5.5 cm at maturity; medium plant height with spreading and prolific branching pattern; average natural season flower date of August 26 in Salinas, Calif. and September 22 in Hightstown, N.J; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of Chrysanthemum, botanically known as *Chrysanthemum morifolium,* Ramat., and referred to by the cultivar name Target.

Target, identified as 82M18012, was originated from a cross made by Grace H. Mack in a controlled breeding program in New Canaan, Conn., in 1981.

The parents of Target were both unnamed seedlings.

Target was discovered and selected as one flowering plant within the progeny of the stated cross by Cornelis P. VandenBerg in September of 1982, in a controlled environment in Salinas, Calif.

The first act of asexual reproduction of Target was accomplished when vegetative cuttings were taken from the initial selection in December of 1982 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Target are firmly fixed and are retained through successive generations of asexual reproduction.

Target has not been observed under all possible environmental conditions. The phenotype may vary significantly with variations in environment such as temperature, light intensity, and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Target, which, in combination, distinguish this Chrysanthemum as a new and distinct cultivar:

1. Flat capitulum form.
2. Decorative capitulum type.
3. Yellow ray floret color.
4. Diameter across face of capitulum up to 5.5 cm at maturity.
5. Medium plant height.

6. Spreading and prolific branching pattern.
7. Average natural season flower date of August 26 in Salinas, Calif., and September 22 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Target, with the colors being as nearly true as possible with illustrations of this type. Sheet 1 is a color photograph of Target grown as a pinched spray pot mum. Sheet 2 is a black and white photograph of three views of the inflorescence of Target. Sheet 3 is a black and white photograph showing the upper and under sides of the leaves of Target at three stages of development (mature, intermediate and immature).

Of the commercial cultivars known to the inventors, the most similar in comparison to Target is Goldmine, disclosed in U.S. Plant Pat. No. 5,661. Reference is made to attached Chart A, which compares certain characteristics of Target to the same characteristics of Goldmine.

Similar traits are ray floret color, capitulum type, average natural season flower date, and controlled flowering response. The capitulum form of Target is more flat, with a larger diameter across face of capitulum than Goldmine. Target has more vigor and a more uniform response than Goldmine.

In the following description, color references are made to The Royal Horticultural Society Colour Chart. The color values were determined on plant material grown in a controlled greenhouse environment in Salinas, Calif. on May 29, 1987.

Classification:

*Botanical.*—*Chrysanthemum morifolium,* Ramat., cv. Target.

*Commercial.*—Decorative spray pot mum and garden mum.

INFLORESCENCE

A. Capitulum:

*Form.*—Flat.

*Type.*—Decorative.

*Diameter across face.*—Up to 5.5 cm at maturity.

B. Corolla of ray florets:

*Color (general tonality from a distance of three meters).*—Yellow.

*Color (upper surface).*—12A.

*Color (under surface).*—12B.

*Shape.*—Oblong, with outer ray florets reflexing.

C. Corolla of disc florets: Not present.

D. Reproductive organs:

*Androecium.*—Not present.

*Gynoecium.*—Present on ray florets.

PLANT

A. General appearance:

*Heights.*—Medium.

*Branching pattern.*—Spreading and prolific.

B. Foliage:

*Color (upper surface).*—147A.

*Color (under surface).*—147B.

*Shape.*—Deeply lobed and slightly serrated.

CHART A

Comparison of Target and Goldmine

| CULTIVAR | RAY FLORET COLOR | CAPITULUM FORM & TYPE | BRANCHING PATTERN |
|---|---|---|---|
| Target | Yellow | Flat Decorative | Spreading and prolific |
| Goldmine | Yellow | Round Pompom | Spreading |

CHART A-continued

Comparison of Target and Goldmine

Decorative

| CULTIVAR | DIAMETER ACROSS FACE OF CAPITULUM | PLANT HEIGHT | CONTROLLED RESPONSE |
|---|---|---|---|
| Target | Up to 5.5 cm | Medium | 7 weeks |
| Goldmine | Up to 4.5 cm | Short | 7 weeks |

| CULTIVAR | AVERAGE NATURAL SEASON FLOWER DATE | |
|---|---|---|
| | SALINAS | HIGHTSTOWN |
| Target | Aug. 26 | Sept. 22 |
| Goldmine | Aug. 27 | Sept. 20 |

COMPARISONS MADE OF PLANTS GROWN UNDER CONTROLLED OUTSIDE CONDITIONS IN SALINAS, CALIFORNIA AND IN HIGHTSTOWN, NEW JERSEY

We claim:

1. A new and distinct Chrysanthemum plant named Target, as described and illustrated, and particularly characterized as to uniqueness by the combined characteristics of flat capitulum form; decorative capitulum type; yellow ray floret color; diameter across face of capitulum of up to 5.5 cm at maturity; medium plant height with spreading and prolific branching pattern; average natural season flower date of August 26 in Salinas, Calif. and September 22 in Hightstown, N.J; uniform seven week photoperiodic flowering response to short days in photoperiodic controlled flowering programs; and durable, uniform performance in outside fall flowerings and in spring small pot flowering programs.

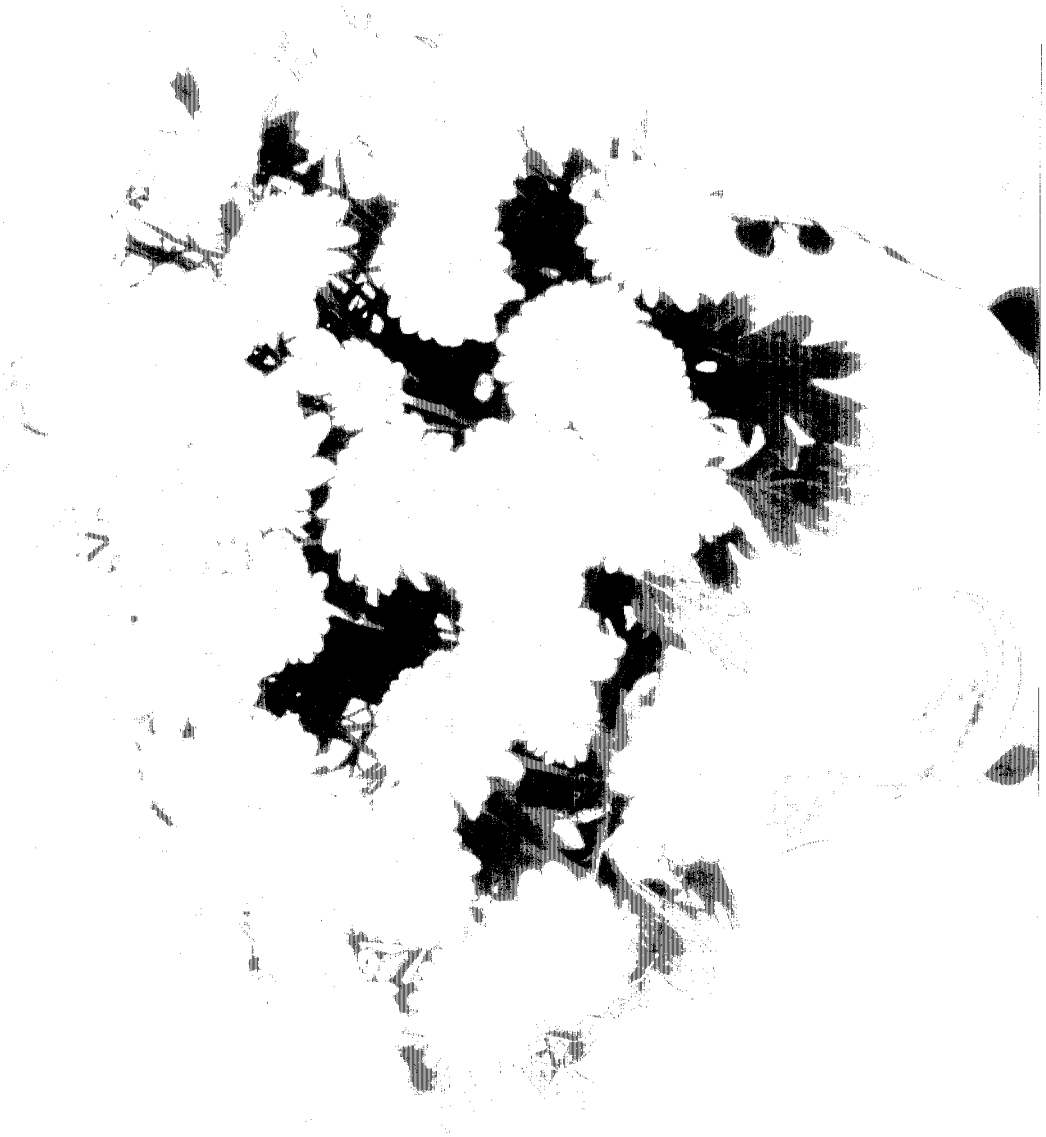

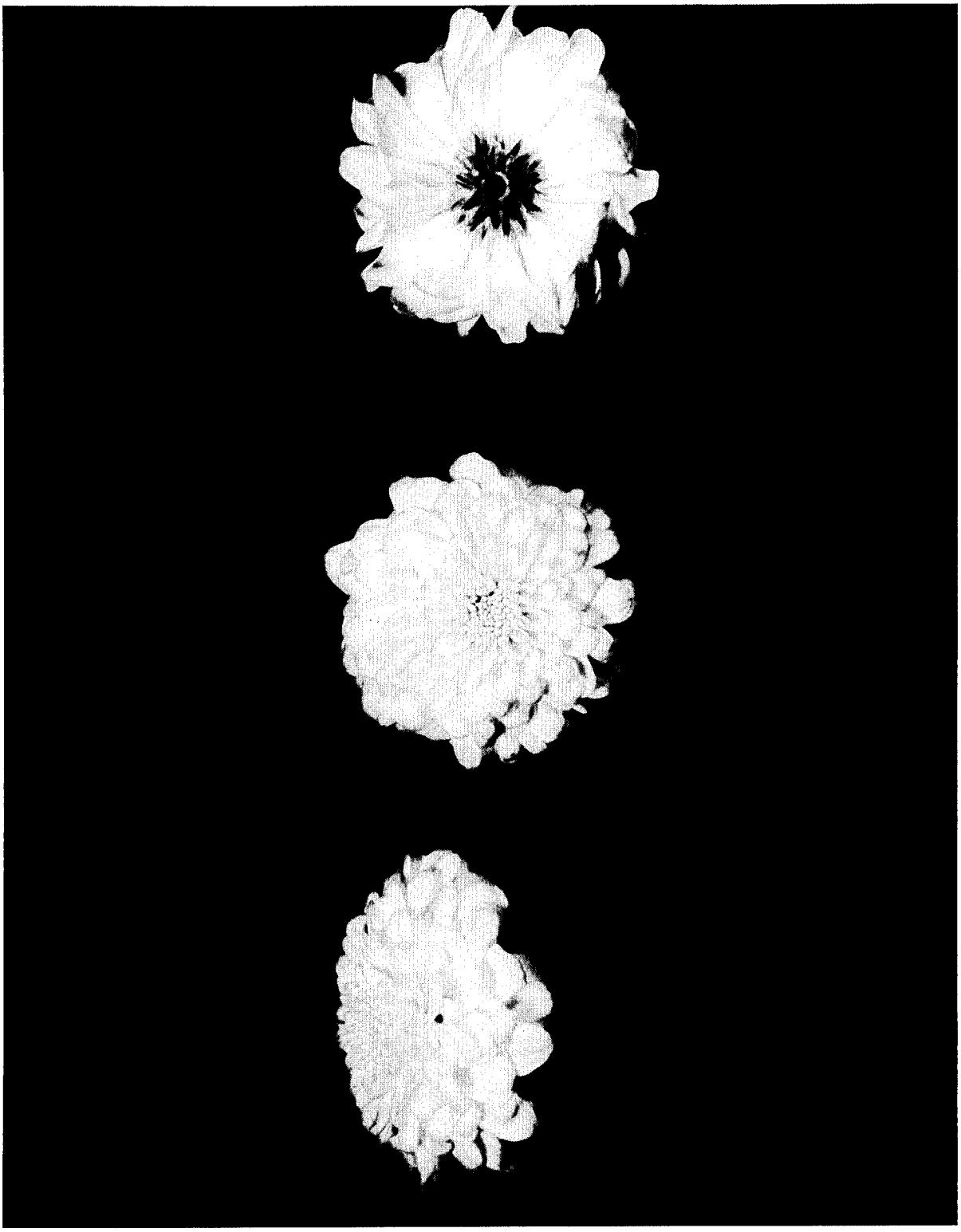

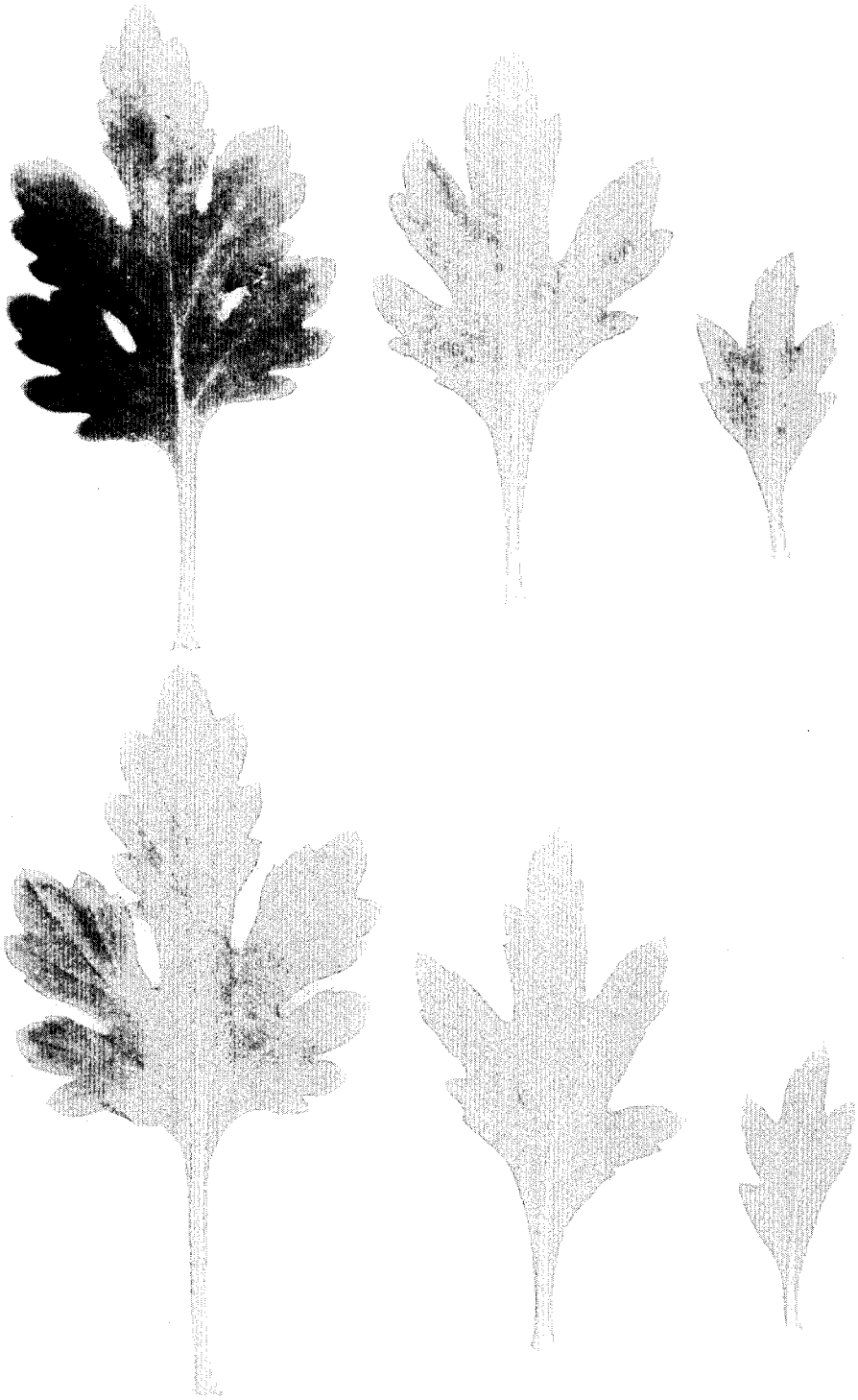

* * * * *